United States Patent [19]

Whitehead et al.

[11] Patent Number: 5,599,700
[45] Date of Patent: Feb. 4, 1997

[54] PROCESS FOR THE PRODUCTION OF CARBOXYLIC ACIDS FROM ALCOHOLS USING SACCHAROMYCES

[75] Inventors: Ian M. Whitehead, Geneva, Switzerland; Eric Ohleyer, Cruseilles, France

[73] Assignee: Firmenich SA, Geneva, Switzerland

[21] Appl. No.: 182,909

[22] Filed: Jan. 13, 1994

Related U.S. Application Data

[63] Continuation-in-part of Ser. No. 64,061, May 18, 1993, abandoned.

[30] Foreign Application Priority Data

Oct. 18, 1991 [CH] Switzerland ................ 3056/91

[51] Int. Cl.[6] ................ C12P 11/00; C12P 7/40; C12P 7/54; C12P 7/52
[52] U.S. Cl. ................ 435/136; 435/130; 435/140; 435/141; 435/247
[58] Field of Search ................ 435/130, 136, 435/247, 140, 141

[56] References Cited

U.S. PATENT DOCUMENTS

| | | | |
|---|---|---|---|
| 4,925,798 | 6/1990 | Hill | 435/136 |
| 5,071,762 | 12/1991 | Shay et al. | 435/247 |

FOREIGN PATENT DOCUMENTS

| | | |
|---|---|---|
| 48-3394 | 1/1973 | Japan . |
| 59-113891 | 6/1984 | Japan . |
| 63-133990 | 6/1988 | Japan . |
| 63-188392 | 8/1988 | Japan . |
| 1588757 | 3/1990 | U.S.S.R. . |

OTHER PUBLICATIONS

Murry W D et al, Dev. Food Sci, 17 (Front–Flavor):1–18 (1988).
"Prescott & Dunn's Industrial Microbiology" ed. G. Reed p. 39 (1982).
"Biotechnology" eds Rehm H–J et al, vol. 6a p. 11 (1988).
Chem Abstracts Fermentations, vol. 79, 1973, p. 235, "2–Furoic acid", Tetsuro Fujishima et al.
Chem Abstracts Microbial Biochem., vol. 113, 1990, p. 329, "Conversion of aromatic and furan compounds during cultiation of microorganisms:", David S. Lester, et al.
Chemical Abstracts, vol. 106, 1987, p. 476, "Microbial oxidation of 1.3–bis(2–hydroxyethoxy)benzene", Toshiro Furukawa, et al.
Chem. Abstracts Fermentations, vol. 101, 1984, p. 539, "Production of monocarboxylic acids from Candida culture", Mitsubishi Rayon Co., Ltd.
Chemical Abstracts, vol. 111, 1989, p. 580, "Enzyme oxidation of alcohols to acids", Nobuo Kato.
Chem Abstracts Fermentations, vol. 77, 1972, p. 313, "Fermentative production of β–methylthiopropionic acid", Kei Arima.
Chem Abstracts Fermentations, vol. 89, 1978, p. 457, "Microbioligical conversion of geraniol and citral", Kasim Cemal Guven et al.
Parfumerie und. Kosmetik, 59. Jahrgang, Nr. Aug. 1978, pag 263, "Microbiological Conversion of Geraniol and Citral", Kasim Cemal Guven, et al.
Agric. Biol. Chem., 48(8), 2017–2023, 1984, p. 2017, "Properties of Formaldehyde Dismutation Catalyzing Enzyme of *Pseudomonas putida* F61", Nobuo Kato, et al.
Archives of Biochemisry and Biophysics 141, 632–640 (1970), p. 632, "A study of Formaldehyde Dismutation by Liver Alcohol Dehydrogenase with NAD +–analogs[1]", Naba K. Gupta.
D'al j. biochem., 20(1971)5–6, 1971, "Oxido–Reduction of Glyoxylate From Crystalline Lactate Dehydrogenase from Rabbit Muscle", M. Romano et al.
Tetrahedron, vol. 42, No. 13, pp. 3351 to 3403, 1986, Tetrahedron Report No. 203, p. 3351, "enzymes in Organic Snthesis", J. Bryan Jones.

*Primary Examiner*—David M. Naff
*Assistant Examiner*—S. Saucier
*Attorney, Agent, or Firm*—Pennie & Edmonds

[57] ABSTRACT

A process for producing carboxylic acids, in particular furoic, 3-methylthio-propionic and 2-methyl-butyric acids, as well as other short-chained, linear and branched acids consisting of the oxidation, in essentially quantitative yields, of the corresponding alcohols or aldehydes using microorganisms of the genera Saccharomyces, Hansenula, Pichia, Candida or Kluyveromyces is disclosed.

14 Claims, No Drawings

PROCESS FOR THE PRODUCTION OF CARBOXYLIC ACIDS FROM ALCOHOLS USING SACCHAROMYCES

CROSS-REFERENCE

This is a continuation-in-part of U.S. application Ser. No. 08/064,061, filed May 18, 1993, now abandoned.

BRIEF SUMMARY OF THE INVENTION

The present invention relates to the field of bioorganic synthesis. More particularly, it concerns a biocatalytic process for the production of carboxylic acids by oxidation of the corresponding alcohols or aldehydes of formula $RCH_2OH$ or $RCHO$ wherein R designates a linear or branched aralkyl, alkyl or alkenyl radical, eventually substituted by a thio-alkyl group, or a furyl or furylalkyl radical, by means of a yeast, wherein said yeast is selected from the group consisting of microorganisms of the Saccharomyces, Hansenula, Pichia, Candida or Kluyveromyces genus and said process comprises:
a. adding, under aerobic conditions, to a prior aerobically cultivated biomass of said yeast a substrate consisting of the appropriate starting alcohol or aldehyde, in an aqueous medium devoid of any carbohydrate source and having a pH comprised between about 7.0–9.0, to obtain essentially quantitative conversion of said starting alcohol or aldehyde into the corresponding carboxylic acid; and
b. extracting said carboxylic acid from the bioconversion medium via conventional methods.

The invention also concerns a process for the microbiological production of 3-methylthio-propionic acid, which comprises:
a. cultivating under aerobic conditions at a pH of about 4.0–5.0 microorganisms of the Saccharomyces genus in the presence of a carbon source and, as sole nitrogen source, L-methionine, to form 3-methylthio-propanol;
b. subsequently allowing the carbon source to become exhausted and adjusting the pH to a value close to 7.0–9.0; and
c. maintaining the resulting suspension under stirring in aerobic conditions for an amount of time sufficient to quantitatively convert the formed 3-methylthio-propanol into the desired corresponding acid.

BACKGROUND OF THE INVENTION

Amongst the compounds whose use is particularly important in the practical flavoring of foods and drinks in general, as well as in perfumery, there appear a great number of carboxylic acids as well as their ester derivatives. Used as such, or as starting materials for obtaining derivatives of varied nature, these acids or esters form a class of compounds for which a constant effort has been invested by the industry in view of their synthesis. Although the microbial production of certain organic acids has been known for a long time—it is enough to think of the formation of acetic acid upon the bacterial production of vinegar—, to this day, there are still no simple and efficient bioconversion methods for preparing carboxylic acids, methods which are of general use. Yet, it is precisely and mostly in certain particular fields such as the pharmaceutical or the food production ones that such microbiological methods are justified.

In industrial practice there are a great number of methods resorting to Saccharomyces cultures, owing to their availability, their low price and their status as approved organisms for the preparation of food ingredients. Therefore, the use of such a family of microorganisms is well documented in the literature.

The same applies to other families of microorganisms such as those of the Hansenula, Pichia, Candida or Kluyveromyces genus.

On the other hand, oxido-reductive dismutation reactions on various substrates have been described in the prior art. For example, it is known that, under the action of the lactate dehydrogenase, glyoxylic acid is converted into oxalic acid and glycolic acid [Ital. J. Biochem., 20 (1971) 129]. The dismutation of formic aldehyde into formic acid and methanol is also known, which dismutation is induced by the alcohol dehydrogenase [Arch. Biochem. and Biophysics, 141 (1970) 632] as well as by microorganisms from the *Pseudomonas putida* family [Agr. Biol. Chem., 48 (1984) 2017].

In spite of this, none of the references found mentions or suggests the use of Saccharomyces, or of yeasts from the Hansenula, Pichia, Candida or Kluyveromyces genus, in efficient and advantageous processes for the preparation of carboxylic acids by quantitative oxidation of the corresponding alcohols or aldehydes.

In fact, in the cases where the prior art has taught the use of fungus or yeasts in similar bioconversions of aldehydes or alcohols, the result has indicated that yeasts are either inefficient microorganisms in this type of bioconversion or need to be grown under conditions which are not convenient for large scale exploitation.

For example, K. C. Güven et al., in Parfümerie und Kosmetik 59, 263 (1978), showed that *Candida krusei* failed to oxidize citral into geranic acid, but produced geraniol instead.

On the other hand, U.S. Pat. No. 5,071,762 which teaches a method for converting short chain alcohols into the corresponding acids by the action of a yeast from the genera Candida, Kluyveromyces, Hansenula, Saccharomyces or Pichia, it was shown that said method required a period of anaerobic fermentation of the yeast, described as physiological or environmental manipulation of the yeast culture, before the bioconversion of the alcohol. In a specific example the authors showed that yeast which had not been manipulated in this manner totally failed to convert butanol into butyric acid. Such a method requires careful monitoring of the amount of ethanol formed during the anaerobic fermentation, which ethanol may easily become toxic to the microorganism being cultivated.

THE INVENTION

We have now discovered a new and simpler process for the bioproduction of carboxylic acids. We have observed that aerobically grown yeasts are perfectly capable of quantitatively oxidizing alcohols and aldehydes into their corresponding acids under certain conditions.

The object of the present invention is therefore a biocatalytic process for the production of carboxylic acids by oxidation of the corresponding alcohols or aldehydes of formula $RCH_2OH$ or $RCHO$ wherein R designates a linear or branched aralkyl, alkyl or alkenyl radical, eventually substituted by a thio-alkyl group, or a furyl or furylalkyl radical, by means of a yeast, wherein said yeast is selected from the group consisting of microorganisms of the Saccharomyces, Hansenula, Pichia, Candida or Kluyveromyces genus and said process comprises:

a. adding, under aerobic conditions, to a prior aerobically cultivated biomass of said yeast a substrate consisting of the appropriate starting alcohol or aldehyde, in an aqueous medium devoid of any carbohydrate source and having a pH comprised between about 7.0–9.0, to obtain essentially quantitative conversion of said starting alcohol or aldehyde into the corresponding carboxylic acid; and b. extracting said carboxylic acid from the bioconversion medium via conventional methods.

In a preferred embodiment, there are used *Saccharomyces cerevisiae* (baker's yeast) as microorganisms, which use renders the process particularly economical. Amongst the preferred microorganisms there are also those of the Hansenula species, in particular the *Hansenula polymorpha*, for example from the ATCC 46059 strain. Examples of other suitable yeasts include *Hansenula polymorpha* ATCC 26012, *Hansenula polymorpha* ATCC 34438, *Hansenula polymorpha* ATCC 14755, *Hansenula polymorpha* CBS 4732, *Kluyveromyces marxianus* ATCC 14424, *Pichia pastoris* ATCC 28485, *Hansenula polymorpha* ATCC 46049, *Candida boidinii* ATCC 32195.

In addition, the efficiency of the process is quite remarkable in a certain number of examples. We have in fact observed that upon the oxidation of furfurol into furoic acid the bioconversion made it possible to obtain concentrations close to 100 g/l of acid in the culture broth. The same applies to the oxidation of 3-methylthio-propanol where concentrations of 45 g/l of the corresponding acid were obtained.

As indicated above, symbol R can represent a linear or branched aralkyl, alkyl or alkenyl radical. Thus, it can designate for example a benzyl, methyl, ethyl, propyl, isopropyl, butyl, isobutyl, tert-butyl, pentyl, hexyl or yet a 2,6-dimethyl-hept-5-en-1-yl and a 2,6-dimethyl-hepta-1,5-dien-1-yl radical. The alkyl radical can be substituted by a thio-alkyl group. Such is the case for example of the 2-thiomethylethyl-ethyl radical.

Among the alcohols that can thus be oxidized into their corresponding acids according to the process of the invention, one can mention by way of example n-butanol, 3-methyl-butanol, isobutanol, 2-methyl-butanol, n-pentanol, n-heptanol, 3-methylthio-propanol, 3,7-dimethyl-6-octen-1-ol (citronellol), geraniol and furfurol, vanillic or cinnamic alcohol.

Among the aldehydes, one can mention n-heptanal, citral and furfural or any of the other aldehydes corresponding to the above-mentioned alcohols.

While the addition of the substrate, consisting of the chosen alcohol or aldehyde, to the yeast is realized preferably at a pH comprised between 7.0 and 9.0, higher pH values can also be used. We have in fact observed that the culture is particularly stable at pH 9.0 or above, as is shown by its ability to oxidize the substrate even after having been kept for several days at this pH.

The process can be carried out using the conventional techniques and apparatus commonly employed in biocatalytic reactions. The biocatalyst can be formed by microorganisms in a free state or in immobilized form.

According to an embodiment of the invention, if necessary, the process comprises a first step of preparation of the yeast through an initial aerating period which consists in suspending the microorganism in water in aerobic conditions, under stirring, at a temperature of about 15° to 35° C. for an amount of time allowing the consumption of their residual supply of carbohydrates. The latter is exhausted when there is no longer consumption of oxygen by the cells. The pH of such a suspension is in the range of about 4.5–6.0. This first step is necessary whenever the yeast culture, as a result for instance of its growth process, possesses a residual supply of carbohydrates, whether endogenous or exogenous or both. For example, the baker's yeast that can be obtained commercially possesses such a supply, as a result of its method of preparation.

It must thus be ensured that the bioconversion medium is devoid of any carbohydrate source. This means that since typically the microorganisms are initially cultured by growing them on a suitable carbon energy source, such as a sugar, under aerobic fermentation conditions in an appropriate growth medium, it is essential that this carbohydrate nutrient source be entirely consumed before the microorganism culture is used in the bioconversion of the alcohol or aldehyde into acid. Examples of such aerobically cultivated microorganisms as required by the invention are given further on.

During the addition of the substrate to the yeast the pH is kept constant by an appropriate titration system.

The process can be carried out through repetitive operations ("batch") or continuously. In the latter case, the formed acid is recovered gradually as it is formed and is separated from the bioconversion medium for example by ultrafiltration and chromatography on a column filled with an ionic exchange resin. The continuous system makes it possible to avoid accumulation of the formed acid, which accumulation, in certain cases and depending on the nature of the acid, could inhibit the reaction.

The present invention has also as an object a particular process for the microbiological production of 3-methylthio-propionic acid by bioconversion of 3-methylthio-propanol (methionol). The latter can be obtained commercially (origin: CTC Organics, Atlanta, Ga.) and used as such in the biocatalytic process of the invention or it can be directly generated in the fermentation vessel from methionine (-D or -L). The invention thus has also as its object a process for the preparation of methylthio-propionic acid, which process comprises two main distinct phases. In the first phase, microorganisms of the Saccharomyces species are grown in the presence of a carbon source, preferably glucose, and of methionine, for example L-methionine, as sole nitrogen source, to form 3-methylthio-propanol in situ.

In the second step, the carbon source is allowed to become exhausted and the pH value of the obtained suspension is adjusted to about 9.0, which provokes the oxidation of 3-methylthio-propanol into the corresponding acid, 3-methylthio-propionic acid.

The present invention thus also relates to a process for the microbiological production of 3-methylthio-propionic acid, which comprises:

a. cultivating under aerobic conditions at a pH of about 4.0–5.0 microorganisms of the Saccharomyces genus in the presence of a carbon source and, as sole nitrogen source, L-methionine, to form 3-methylthio-propanol;

b. subsequently allowing the carbon source to become exhausted and adjusting the pH to a value dose to 7.0–9.0; and c. maintaining the resulting suspension under stirring in aerobic conditions for an amount of time sufficient to quantitatively convert the formed 3-methylthio-propanol into the desired corresponding acid.

The acid thus formed can be separated from the bioconversion medium by means of the usual techniques such as mentioned above.

Also in this case, the bioconversion of L-methionine into 3-methylthio-propionic acid can be carried out by means of a conventional apparatus. As feeding substrate, there are used, as adjuvants to the carbohydrate source and L-methionine, salts such as potassium phosphate, magnesium sulfate, calcium chloride, iron$^{II}$ sulfate, zinc sulfate, manganese sulfate and copper$^{II}$ sulfate. Biotin can also be added to this nutritive medium.

As biocatalyst, microorganisms of the Saccharomyces species, in particular *Saccharomyces cerevisiae* or baker's yeast such as available commercially, can be used. Other microorganisms, namely those of the Hansenula or Pichia species, turned out to be just as appropriate.

Variable concentrations of these microorganisms can be employed. The same applies to the proportions of the feeding substrate. Thus, the amounts of pressed yeast can vary between about 5 and 50% by weight in the culture medium. As regards the nutritive solution, it can be conveniently added to the culture medium by a system of gradual incorporation. In practice, one proceeds by putting the suspension of baker's yeast in an aqueous solution containing an initial mixture of feeding substrate. After adjusting the pH to about 4.5, the resulting suspension is kept under stirring in appropriate aerobic conditions, ensured by controlled introduction of an air flow. The desired growth regime is then reached by gradual addition of a solution containing the carbohydrate and the L-methionine. Such a solution preferably contains about 50% of glucose and 3–5% of L-methionine.

Finally, after complete bioconversion of the methionine into 3-methylthio-propanol, the addition of the feeding solution is interrupted and the carbon source allowed to be exhausted and the pH is adjusted to about 9.0. Under these conditions, the fermentation continues with the conversion of 3-methylthio-propanol into 3-methylthio-propionic acid.

The invention is described in further detail by way of the following examples wherein the temperatures are indicated in degrees centigrade and the abbreviations have the usual meaning in the art. All the microorganisms used can be obtained commercially.

EXAMPLE 1

General Experimental Method

In order to establish the best experimental conditions, the preparation of the carboxylic acids was carried out as follows.

A suspension of 500 ml of pressed baker's yeast at 20% in water was kept for one night at 30° under stirring in a 1 l. Erlenmeyer flask in aerobic conditions. Then, 50 ml of this suspension were put into a 125 ml Erlenmeyer flask and 2 g calcium carbonate were added thereto so as to adjust the pH at about 7.0; then, 50 mg of the chosen substrate, alcohol or aldehyde, were added to the resulting mixture and the whole was stirred until the reaction was complete. The evolution of the reaction was followed by regular sampling of 1 ml aliquots.

The latter were centrifuged so as to obtain a clear liquid. Samples of this liquid (500 µl) were acidified with 50 µl of 5N HCl and extracted with 500 µl of ethyl acetate in an Eppendorf tube. The organic phase was analyzed by gas chromatography by means of a mod. SPB1 column [origin: Supelco]. Proceeding as described above, there were prepared the carboxylic acids designated in the following table:

| Starting product | Carboxylic acid |
| --- | --- |
| Alcohols | |
| Isobutanol | isobutyric ac. |
| 2-Methyl-butanol | 2-methyl-butyric ac. |
| 3-Methyl-butanol | 3-methyl-butyric ac. |
| n-Pentanol | pentanoic ac. |
| n-Heptanol | heptanoic ac. |
| 3-Methylthio-propanol | 3-methylthio-propionic ac. |
| Citronellol | 3,7-dimethyl-oct-6-en-1-oic ac. |
| Geraniol | geranic ac. |
| Furfurol | furoic ac. |
| Vanillic alcohol | vanillic ac. |
| Cinnamic alcohol | cinnamic ac. |
| Aldehydes | |
| n-Heptanal | n-heptanoic ac. |
| Citral | geranic ac. |
| Furfural | furoic ac. |

The nature of the products obtained was determined by comparing with commercial pure samples.

Amongst the substrates tested as indicated above, the following compounds were chosen for bioconversion in a fermentor: isobutanol, 2-methylbutanol, 3-methylthio-propanol, heptanal, furfural and furfurol. The method followed is described hereinafter by way of example for the production of furoic acid.

800 ml of a 20% pressed baker's yeast suspension (weight/volume) in water were kept at 30° under stirring for one night (1300 rpm) in a 1 l 5 neck reactor equipped with a turbine (Medimex), a pH titrator, an air input tube (2.5 v/v/m) and a condenser. The pH was then increased from 3.5 to 9.0 by the addition of 4.85 mM of soda over an interval of about 10 min. The pH was kept at the indicated value by gradual addition of soda, and this during several hours, then, 70 ml (0.81M) of furfurol were introduced into the reactor by successive aliquots of 10 ml. The addition took place at 0, 3, 8, 23, 27, 31 and 47 hours.

After 62 h the reaction mixture (850 ml) was centrifuged to yield 705 ml of a brown clear liquid which was acidified with 85 ml of conc. HCl, which provoked the precipitation of the desired acid. Through filtration and vacuum drying, there were obtained 52.2 g of a slightly brown amorphous solid. The aqueous phase was extracted with ether (2×700 ml), then the ethereal part was dried over MgSO$_4$ and evaporated to yield an additional fraction of 24.3 g of furoic acid.

The isolated acid was identical to an analytical sample obtained from a commercial product.

EXAMPLE 2

An initial fermentation mixture was prepared by admixing the following ingredients:

250 g of pressed baker's yeast 100 g of L-methionine 10 g of glucose monohydrate 15 g of KH$_2$PO$_4$ 7.5 g of MgSO$_4$.7H$_2$O 5 g of CaCl$_2$.2H$_2$O 0.33 g of FeSO$_4$.7H$_2$O 0.1 g of ZnSO$_4$.7H$_2$O 0.02 g of MnSO$_4$.H$_2$O 0.03 g of CuSO$_4$.5H$_2$O 0.2 g of biotin
4.52 l of water.

This mixture was placed in a fermentor at 30°. The pH was adjusted at 4.5 and kept at this value by the addition of a 30% soda solution, while an air flow (10 l/min) was introduced into the stirred suspension (about 300–500 rpm).

A feeding solution of glucose monohydrate and L-methionine was then gradually added to the mixture at the following intervals and in the following amounts:

| Time | Solution | Quantity [l] | Speed of addition [ml/h] |
|---|---|---|---|
| 0–15 h | 50% glucose | 1.0 | 66.7 |
| 16–60 h | 50% glucose + 3.33% L-methionine | 3.0 | 66.7 |
| 61–95 h | 50% glucose | 2.34 | 66.7 |

The addition of the glucose and 1-methionine solution was stopped and the pH was taken to about 9.0, then the fermentation was continued for 88 h. The mixture thus obtained (9.75 kg) was centrifuged to yield 8.64 l of a brown clear liquid from which an aliquot of 500 ml was extracted with ethyl acetate (2×500 ml), then the aqueous phase was acidified at pH 1 with conc. HCl and again extracted with two fractions (500 ml) of ethyl acetate.

The organic extracts were washed with a saline solution, dried over anhydrous $MgSO_4$ and filtered. By evaporating the solvent, there were obtained as a residue 9.1 g of a dark oil, which, by distillation in a bulb-to-bulb apparatus, yielded 5.64 g of 3-methylthio-propionic acid.

The analytical characteristics of the obtained acid were identical in all respects to those of an analytical sample prepared from a commercial product.

EXAMPLE 3

Oxidation of Isoamylic Alcohol by Means of *Hansenula polymorpha*

1. Fermentation

A biological mass of *Hansenula polymorpha* ATCC 46059 was obtained by aerobic fermentation using the following culture medium [g/l]:

| | |
|---|---|
| glucose monohydrate | 25 |
| yeast extract | 10 |
| peptone | 10 |
| $KH_2PO_4$ | 5 |
| NaCl | 2 |

15 l of this mixture were placed in a fermentor equipped with an aeration input (5 v/v/m) and the pH was adjusted at 7.0 while the temperature was taken to 37°. Fermentation was allowed to continue until complete exhaustion of the glucose, detected through measuring the glucose content of the medium. The wet biological mass was recovered by centrifugation, then the cells were washed once with distilled water and centrifuged again. They were thus ready for the following bioconversion step.

2. Bioconversion

The bioconversion with the resting cells is carried out at room temperature in water with 10% of wet biomass and 0.01% of 3-methylbutanol.

The progress of the bioconversion was followed by chromatographic analysis of reaction medium samples after extraction with ether. The reaction is continued during 6 days. The isovalerianic acid is thus obtained with a conversion of 90%.

EXAMPLE 4

Proceeding in a manner similar to that described in Example 3, the alcohols designated in the following table were quantitatively converted into the corresponding acids by means of the microorganisms indicated in the table. Said microorganisms had been aerobically cultivated in a growth medium as indicated in Example 3, in a similar manner to that there-described, before being used in the bioconversion of the alcohol into acid.

| Starting alcohol | Microorganism |
|---|---|
| n-Butanol | *Hansenula polymorpha* ATCC 26012 |
| | *Hansenula polymorpha* ATCC 34438 |
| | *Hansenula polymorpha* ATCC 14755 |
| | *Hansenula polymorpha* CBS 4732 |
| | *Kluyveromyces marxianus* ATCC 14424 |
| Isobutanol | *Hansenula polymorpha* ATCC 14755 |
| | *Pichia pastoris* ATCC 28485 |
| 3-Methyl-butanol | *Hansenula polymorpha* ATCC 46049 |
| n-Pentanol | *Hansenula polymorpha* ATCC 34438 |
| | *Candida boidinii* ATCC 32195 |
| Geraniol | *Hansenula polymorpha* ATCC 14755 |

What we claim is:

1. A biocatalytic process for the production of carboxylic acids by oxidation of the corresponding alcohols, which process comprises the steps of:

(a) suspending, under aerobic conditions, in an aqueous medium at a temperature of about 15° to 35° C. and a pH of about 4.5 to 6, a biomass of a yeast of genus Saccharomyces for an amount of time sufficient to consume all of the yeast's residual carbon nutrient supply, to form an aqueous bioconversion medium devoid of any carbon nutrient source;

(b) adding buffer to the formed aqueous bioconversion medium to adjust the pH of said medium to a value of between about 7 and 9 and subsequently continuing the addition of the buffer to maintain said pH value constantly at between about 7 and 9;

(c) adding a substrate to the thus obtained buffered aqueous bioconversion medium, said substrate selected from the group consisting of ethanol, propanol, 2-methyl-1-propanol, 2,2-dimethyl-1-propanol, n-butanol, isobutanol, 2-methyl-butanol, 3-methyl-butanol, n-pentanol, n-hexanol, n-heptanol, and 3-methylthio-propanol, and contacting said substrate with the biomass of the yeast in the buffered bioconversion medium for an amount of time sufficient to convert said substrate into the corresponding carboxylic acid and to form the latter acid in essentially quantitative yield in the bioconversion medium; and (d) extracting the formed carboxylic acid from the bioconversion medium via conventional methods.

2. A process according to claim 1, wherein said buffer is added to the formed aqueous bioconversion medium in step (b) to adjust and maintain the pH of said bioconversion medium at about 9 and wherein the pH of the aqueous bioconversion medium in step (c) is about 9.

3. A process according to claim 1, wherein the formed carboxylic acid is extracted from the bioconversion medium by a continuous system that comprises ultrafiltration and ionic exchange chromatography.

4. A process according to claim 1, wherein the yeast is *Saccharomyces cerevisiae.*

5. A process according to claim 4, wherein the formed carboxylic acid is extracted from the bioconversion medium by a continuous system that comprises ultrafiltration and ionic exchange chromatography.

6. A process according to claim 4, wherein the buffer is added to the formed aqueous bioconversion medium in step (b) to adjust and maintain the pH of said medium at about 9 and wherein the pH of the aqueous bioconversion medium in step (c) is about 9.

7. A process according to claim 6, wherein the formed carboxylic acid is extracted from the bioconversion medium by a continuous system that comprises ultrafiltration and ionic exchange chromatography.

8. A process according to claim 1, wherein the substrate is selected from the group consisting of n-butanol, 2-methyl-butanol, 3-methyl-butanol, isobutanol, n-pentanol, n-hexanol, n-heptanol and their corresponding aldehydes.

9. A process according to claim 6, wherein the buffer is added to the formed aqueous bioconversion medium in step (b) to adjust and maintain the pH of said medium at about 9 and wherein the pH of the aqueous bioconversion medium in step (c) is about 9.

10. A process according to claim 8, wherein the formed carboxylic acid is extracted from the bioconversion medium by a continuous system that comprises ultrafiltration and ionic exchange chromatography.

11. A process according to claim 8, wherein the yeast is *Saccharomyces cerevisiae.*

12. A process according to claim 11, wherein the formed carboxylic acid is extracted from the bioconversion medium by a continuous system that comprises ultrafiltration and ionic exchange chromatography.

13. A process according to claim 11, wherein the buffer is added to the formed aqueous bioconversion medium in step (b) to adjust and maintain the pH of said medium at about 9 and wherein the pH of the aqueous bioconversion medium in step (c) is about 9.

14. A process according to claim 13, wherein the formed carboxylic acid is extracted from the bioconversion medium by a continuous system that comprises ultrafiltration and ionic exchange chromatography.

\* \* \* \* \*

UNITED STATES PATENT AND TRADEMARK OFFICE
CERTIFICATE OF CORRECTION

PATENT NO. : 5,599,700

DATED : February 4, 1997

INVENTOR(S) : I. Whitehead et al.

It is certified that error appears in the above-identified patent and that said Letters Patent is hereby corrected as shown below:

Claim 9 should depend from claim 8.

Signed and Sealed this

Twenty-fourth Day of June, 1997

Attest:

BRUCE LEHMAN

Attesting Officer

Commissioner of Patents and Trademarks